United States Patent [19]

Bauman

[11] 4,123,516

[45] Oct. 31, 1978

[54] QUATERNARY COMPOUNDS HAVING ANTI-MICROBIAL ACTIVITY

[75] Inventor: Robert A. Bauman, New Brunswick, N.J.

[73] Assignee: Colgate-Palmolive Company, New York, N.Y.

[21] Appl. No.: 802,760

[22] Filed: Jun. 2, 1977

Related U.S. Application Data

[60] Division of Ser. No. 606,138, Aug. 20, 1975, abandoned, which is a division of Ser. No. 400,097, Sep. 24, 1973, Pat. No. 3,928,411, which is a continuation of Ser. No. 39,536, May 21, 1970, abandoned.

[51] Int. Cl.$^2$ .................. A61K 7/22; A61K 31/215
[52] U.S. Cl. .................. 424/54; 424/305; 424/329; 560/117

[58] Field of Search .................. 424/54, 305; 560/117

[56] References Cited

U.S. PATENT DOCUMENTS

| 3,374,244 | 3/1968 | Krimmel | 260/326.3 |
| 3,565,942 | 2/1971 | Krimmel | 260/468 |

*Primary Examiner*—Leonard Schenkman
*Attorney, Agent, or Firm*—Robert L. Stone; Murray M. Grill; Herbert S. Sylvester

[57] ABSTRACT

Anti-microbial quaternary ammonium compounds which include the adamantane ring system linked to the quaternary ammonium group by a hydrocarbon chain or by other functional groups, such as ether, carboxylic ester, carboxamide, keto, carbamate ester, thiocarbamate ester, etc.

6 Claims, No Drawings

QUATERNARY COMPOUNDS HAVING ANTI-MICROBIAL ACTIVITY

This is a divisional of application Ser. No. 606,138, filed Aug. 20, 1975, now abandoned, which was a division of Ser. No. 400,097, filed Sept. 24, 1973, now U.S. Pat. No. 3,928,411, issued Dec. 23, 1975, which is a continuation of Ser. No. 39,536, filed May 21, 1970, now abandoned.

The present invention relates to novel quaternary ammonium compounds represented by the general formula:

$$[RZ(CH_2)_n N^+(CH_3)_2 R^1] X^-$$

wherein R is 1-adamantyl ($C_{10}H_{15}$), $R^1$ is a long chain alkyl group of 10 – 18 carbon atoms, Z is selected from the group consisting of [$CH_2$, O, S, C=O, COO, CONH, CHOH, NHCOO, and NHCSO.], $n$ is an integer from 1 to 3 and X is a compatible anion. These quaternary compounds possess superior anti-microbial, anti-caries and anti-calculus activity.

The adamantyl radical is derived from tricyclo-[3.3.1.1³,7] decane showing four trans cyclohexane rings as follows:

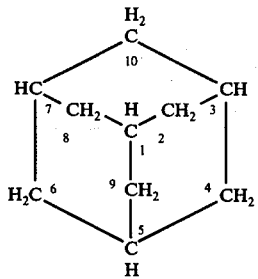

Typical examples of the quaternary ammonium compounds which may be used in this invention are:

2-(1'-adamantanecarbonyloxy)ethyldimethyldecyclammoniumbromide, 2-(1'-adamantanecarbonyloxy)ethyldimethyltetradecylammonium bromide, 3-(1'-adamantanecarboxamido)propyldimethyldodecylammonium bromide, 3-(1'adamantanecarboxamido)propyldimethyltetradecylammonium bromide, 1-adamantyloxyethyldimethyltetradecylammonium bromide 1-adamantyloxyethyldimethyldodecylammonium bromide 1-adamantylcarbonylmethyldimethyltetradecylammonium bromide 1-adamantylcarbonylmethyldimethyldodecylammonium bromide 2-(1'-adamantylthiocarbamyloxy)ethldimethyldodecylammonium adamantylthiocarbamyloxy)ethyldimethyldodecylammonium The halides such as the chlorides, fluorides and analogous compounds may also be employed herein as effective anti-bacterials.

it has been observed that the compounds generally described by the foregoing formula are particularly effective against gram positive organisms such as *Staphylococcus aureus, Streptococcus mitis, Bacillus subtilis, Corynebacterium acnes,* and against fungi, such as *Candida albicans, Trichophyton mentogrophytes* and *Aspergillus niger,* and moderately effective against *Escerichia coli* which is a gram negative bacteria. Compounds wherein $R^1$ is a benzyl radical in lieu of instant higher alkyl radical are devoid of antibacterial activity.

The anti-microbial nature of the instant novel compounds was shown by a standard test tube serial dilution test in which an appropriate number of test tubes of broth containing decreasing concentrations of the test agent was inoculated with the test organism. After a suitable period of incubation the tubes were examined for the presence or absence of growth. The activity of the test agent was the lowest concentration which inhibited the growth of the organism and is expressed as the minimal inhibitory concentration in $\mu g/ml$.

TABLE I

| | | | | Minimum Inhibitory Concentration (ug/ml) | | | | | | | |
|---|---|---|---|---|---|---|---|---|---|---|---|
| R | Z | R' | n | S. aureus | S.mitis | B.subtilis | C.acnes | C.albicans | T.mentagrophytes | A.niger | E.coli |
| Adamantyl | COO | $C_{10}H_{21}$ | 2 | 1.56 | 6.25 | 1.56 | 1.56 | 12.5 | 7.8 | 31.2 | 25 |
| Adamantyl | COO | $C_{12}H_{25}$ | 2 | .02 | .19 | .19 | 6.25 | .78 | 6.25 | 50 | 12.5 |
| Adamantyl | COO | $C_{14}H_{29}$ | 2 | .78 | .78 | .1 | 25. | 6.25 | 25 | 50 | 50 |
| Adamantyl | CONH | $C_{12}H_{25}$ | 3 | .78 | .39 | — | — | 6.25 | 12.5 | 25 | 50 |
| Adamantyl | CONH | $C_{14}H_{29}$ | 3 | .39 | .39 | — | — | 6.25 | 25 | 50 | 25 |
| Adamantyl | O | $C_{12}H_{25}$ | 2 | .39 | .19 | — | — | 1.56 | 3.12 | 50 | 12.5 |
| Adamantyl | O | $C_{14}H_{29}$ | 2 | .78 | .39 | — | — | 1.56 | 6.25 | 50 | 12.5 |
| Adamantyl | NHCSO | $C_{12}H_{25}$ | 2 | 1.56 | .78 | .39 | 12.5 | 6.25 | 3.9 | 62.5 | 25 |

These dilution tests evidence the effectiveness of compounds of the invention against bacteria and fungi.

When used against bacteria or fungi, compounds of the instant invention may be applied directly to the surface to be protected or may be dissolved in a pharmaceutical carrier. Typically, an effective amount, e.g. 0.1 to about 10% by weight of the compound, is included in an inert carrier and a dispersing or surface active agent. Alternatively, an effective amount, e.g. 0.1 to about 10% by weight may be incorporated into a solid carrier which may be inert, such as talc, clay, diatomaceous earth, flour, etc.

The quaternary ammonium amides of adamantyl carboxylic acid are particularly effective in inhibiting the development of dental calculus as shown by the results of tests on litter-mated albino rats, in groups of 15 males and 15 females who were fed a Zipkin-McClure calculus producing diet. For 6 weeks the teeth of each animal were swabbed for 30 seconds each day with a test solution or water for the control group. The animals were then sacrificed, defleshed and scored by Baer's method for calculus. The results were analyzed by Student's "t" test and in the results quoted were 99% significant.

| Compound | Concentration Test Solution | Calculus Reduction % | |
|---|---|---|---|
| | | Males | Females |
| 3-(1'-adamantane-carboxamido) propyl tetradecyl dimethyl ammonium | .1% | 43.43 | 6.27 |

| Compound | Concentration Test Solution | Calculus Reduction % Males | Females |
|---|---|---|---|
| bromide | | | |

The results set forth above indicate the significant effectiveness of the quaternary compounds of the invention in inhibiting formation of oral calculus in concentrations as low as 0.1%.

When compounds of the instant invention are intended for use in compositions which reduce formation of caries and inhibit formation of oral calculus, they are typically incorpoated in oral preparation in effective amounts up to about 5% by weight, preferably 0.1-1% and most preferably 0.25-0.5% by weight of the oral preparation. Typically, the oral preparation is a dentrifrice, such as a dental cream, tablet or powder, containing as a vehicle about 20-95% by weight of a water-insoluble polishing material, preferably including water-insoluble phosphate such as dicalcium phosphate, tricalcium phosphate, trimagnesium phosphate. The dentrifrice may also include water; binders such as glycerine, sorbitol, propylene glycol, and polyethylene glycol 400; detergents; gelling agents such as Irish moss and sodium carboxymethyl cellulose; additional antibacterial agents; coloring or whitening agents; preservatives; silicones; chlorophyll compounds; additional ammoniated materials; flavoring or sweetening materials; and compounds which provide fluorine-containing ion such as sodium fluoride, stannous fluoride and sodium monofluorophosphate.

The oral preparation may also be a liquid such as mouth rinse which typically contains 20-99% by weight of an aqueous alcohol such as ethanol, n-propyl, or isopropyl alcohol and being present in amount of about 5-30% by weight of the oral preparation.

Such oral preparations are typically applied by brushing the teeth or rinsing the oral cavity for 30-90 seconds at least once daily. Typical oral preparations of the invention which can be applied in this manner are set forth below.

EXAMPLE 1

| Dental-Cream | % |
|---|---|
| Quaternary ammonium ester of adamantyl carboxylic acid | 0.50 |
| Nonionic detergent* | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.75 |
| Flavor | 0.80 |
| Water | 22.15 |

*Tween 80 - Polyoxyethylene (20 moles ethylene oxide) sorbitan monooleate.

EXAMPLE 2

| Mouthwash | % |
|---|---|
| Quaternary ammonium amide of adamantyl carboxylic acid | 0.25 |
| Nonionic detergent (Pluronic F-68)* | 1.00 |
| Ethyl alcohol (containing flavor) | 15.00 |
| Glycerine | 10.00 |
| Saccharin | 0.02 |
| Water | 73.75 |

*Block polymer of 80% polyoxyethylene and 20% polyoxypropylene

The quaternary ammonium esters of adamantane carboxylic acid can be prepared by a two-step process of reacting adamantanecarboxylic acid chloride with a dimethylaminoethanol to form the carboxylate, followed by quaternizing with an alkyl halide as illustrated by the following equations:

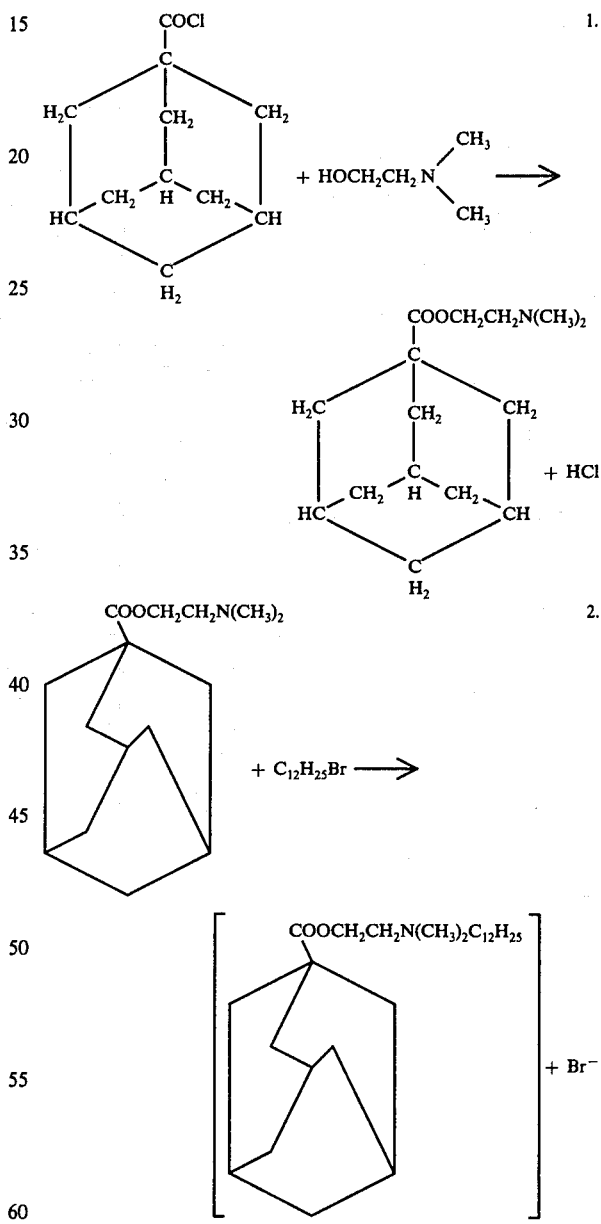

The quaternary ammonium amides of adamantanecarboxylic acid can also be prepared by a two-step method of reacting the adamantanecarboxylic acid chloride with a dimethyl diamine and subsequently quaternizing with an alkyl halide.

Similarly, the quaternary ammonium compounds of this invention, represented by the following formulae:

[RO(CH₂)ₙN⁺(CH₃)₂R']X

[RCO(CH₂)ₙN⁺(CH₃)₂R']X

[RNHCSO(CH₂)ₙN⁺(CH₃)₂R']X

[RS(CH₂)ₙN⁺(CH₃)₂R']X⁻

[RNHCOO(CH₂)ₙN⁺(CH₃)₂R']X⁻

[RCHOH(CH₂)ₙN⁺(CH₃)₂R']X

[RCH₂(CH₂)ₙN³⁰(CH₃)₂R'']X⁻ wherein R, R', n and X have the same designations as in the general formula, can also be prepared by a similar two-step method of reacting a compound containing the adamantane radical with a compound containing the dimethyl amine radical and then quaternizing with a higher aliphatic halide.

The following examples illustrate the manner in which compounds of this invention are prepared.

EXAMPLE 3

Preparation of 2-(1'-adamantanecarbonyloxy)ethyldimethyldodecylammonium bromide

A solution of 21.7g (0.11 mole) 1-adamantanecarboxylic acid chloride in 100 ml. ether was added to a solution of 19.4g. (0.22 mole) 2-dimethylaminoethanol in 200 ml. ether. The reaction mixture was stirred overnight at room temperature. Since unreacted acid chloride could still be detected by infrared spectrum, additional 15g. (0.17 mole) 2-dimethylaminoethanol was added and the reaction mixture again stirred overnight. The reaction mixture was poured into 300 ml. water and treated with 20 ml. of 10% NaOH solution. From the ether layer was recovered 23g. of oil with an infrared spectrum compatible with the proposed structure of 2-Dimethylaminoethyl 1-adamantanecarboxylate.
Analysis: Calculated for $C_{15}H_{25}NO_2$: C, 71.67; H, 10.02. Found: C, 71.26, H, 9.94.

Ten grams (0.04 mole) of the product of step 1 was mixed with 10g. (0.04 mole) 1-bromododecane and allowed to stand for 6 weeks. The resultant crystalline mass was washed with ether and dried to 17.5g. white crystals (88% of theory). Two recrystallizations from ethyl acetate gave 15.6g. white crystals having a melting point of 176°–178° C.

| Analysis: | Found | Calculated |
|---|---|---|
| Carbon | 64.95 | 64.78 |
| Hydrogen | 10.15 | 10.07 |

EXAMPLE 4

The decyl homolog of the above carboxylate, i.e., where R' is $C_{10}H_{21}$, was prepared similarly to Example 3. The recovered crystals had a melting point of 183°–184.5° C and the following analysis:

| | Found | Calculated |
|---|---|---|
| Carbon | 63.00 | 63.54 |
| Hydrogen | 9.90 | 9.81 |

EXAMPLE 5

The tetradecyl homolog was prepared in accordance with the process defined in Example 3, yielding crystals having a melting point of 176° – 178° C with the following analysis:

| | Found | Calculated |
|---|---|---|
| Carbon | 65.33 | 65.89 |
| Hydrogen | 10.18 | 10.30 |

EXAMPLE 6

Preparation of 3-(1'-adamantanecarboxamido)propyldodecyldimethylammonium bromide: 2.5 grams of N,N-dimethyl-1,3-propane diamine was added to a cold solution of 5 grams 1-adamantane carboxylic acid chloride in 15cc benzene. An immediate precipitate formed. The mixture was stirred and permitted to sit for 30 minutes. The precipitate was washed with benzene several times, centrifuged, and dried in vacuum, yielding 5 grams of N-(3-dimethylaminopropyl) adamantane 1-carboxamide hydrochloride having a melting point of 154°–157° C. This product was dissolved in 150cc acetone, placed in a refrigerator for crystal growth and 4.8 gms of the product was recovered.

This hydrochloride was dissolved in 100cc water and 25cc of 1N NaCH was added. A white precipitate formed which was extracted with ether, dried by flash evaporation and 3.2 grams of the free base having a melting point of 78°–80° C was recovered. The infrared spectrum confirmed the structure of this product.

The aforedefined reaction product was quaternized by reacting 1.6 grams (.06 mole) of N-(3-dimethylaminopropyl) -1-adamantanecarboxamide with 1.5 grams (.06 mole) of 1-bromododecane dissolved in 4cc acetone. After standing for 2 weeks the reaction mixture was chilled with dry ice. The resultant crystalline mass was washed with ether, dried in vacuum and recrystallized from ethyl acetate, giving a crystalline product having a melting point of 122°–124° C and the following analysis:

| | Found | Calculated |
|---|---|---|
| Carbon | 64.81 | 65.47 |
| Hydrogen | 10.84 | 10.40 |
| Molecular weight: 513.66 | | |

EXAMPLE 7

The tetradecyl homolog of the above carboxyamide was prepared in accordance with the process of Example 6. The recovered crystals had a melting point of 120°–122° C and the following analysis:

| | Found | Calculated |
|---|---|---|
| Carbon | 65.80 | 66.52 |
| Hydrogen | 10.54 | 10.61 |
| Molecular weight 541.71 | | |

EXAMPLE 8

Preparation of 1-adamantyloxyethyldimethyltetradecylammonium bromide

A mixture of 3.6g (0.015 mole) 1-(2'-dimethylaminoethoxy) adamantane [prepared by the method of Charkrabarti, Faulis and Szinai, Tetrahedron Letters, No. 60, 6249 (1968)] and 4.3g (0.05 mole) 1-bromotetradecane was prepared and allowed to stand at room temperature for 6 days. The resultant solid was recrystallized from 30cc ethyl acetate to 4.75g white crystals. After recrystallization it melted at 132°–135°.

|  | Found | Calculated |
|---|---|---|
| Carbon | 67.32 | 67.17 |
| Hydrogen | 10.96 | 10.87 |
| Bromine | 15.92 | 15.96 |

EXAMPLE 9

The dodecyl homolog was prepared by the procedure of Example 8, yielding hygroscopic crystals having a melting point when dry of 128°–130° and the following analysis:

|  | Found | Calculated |
|---|---|---|
| Bromine | 16.91 | 16.91 |

EXAMPLE 10

Preparation of 1-adamantylcarbonylmethyldimethyltetradecylammonium bromide

A mixture of 1.3g. (0.005 mole) 1-adamantyl bromomethyl ketone and 1.23g (0.005 mole) dimethyltetradecylamine was solubilized by the addition of 30cc acetone. The next day the solidified mixture was washed with ether and recrystallized from ethyl acetate to yield 2.1g white crystals, m.p. 134°–135.5°.

|  | Found | Calculated |
|---|---|---|
| Carbon | 67.72 | 67.45 |
| Hydrogen | 10.65 | 10.51 |

EXAMPLE 11

The dodecyl homolog was prepared by the procedure of Example 10 yielding white crystals of melting point 140°–141.5° and with the following analysis.

|  | Found | Calculated |
|---|---|---|
| Carbon | 66.55 | 66.36 |
| Hydrogen | 9.87 | 10.28 |

EXAMPLE 12

2-(1'-adamantylthiocarbamyloxy)ethyldimethyldodecylammonium bromide was prepared by a two-step process. First, 1-adamantyl isothiocyanate was reacted with the sodium derivative of 2-dimethylaminoethanol. The product after recrystallization from ethylacetate and from hexane had a melting point of 86°–88.5° and an analysis of

|  | Found | Calculated |
|---|---|---|
| Carbon | 64.02 | 63.79 |
| Hydrogen | 9.41 | 9.28 |

A solution of 4.5g of the above-prepared 0-(2-dimethylaminoethyl 1-adamantylthiocarbamate and 4.0g 1-bromododecane in 15cc acetone was allowed to stand for 4 days. The product was recrystallized from ethylacetate and from acetone in white crystals, m.p. 143°–143.5° and had the following analysis

|  | Found | Calculated |
|---|---|---|
| Carbon | 61.04 | 60.99 |
| Hydrogen | 9.65 | 9.67 |

Although this invention has been described with reference to specific examples, it will be apparent to one skilled in the art that various modifications may be made thereto which fall within its scope.

What is claimed is:

1. anti anti-microbial pharmaceutical composition comprising about 0.1–10% by weight of a chemical compound having the structural formula

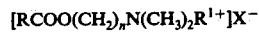

wherein R is 1-adamantyl, $R^1$ is a long chain alkyl group of 10 to 18 carbon atoms, n is an integer from 1 to 3 and X is a compatible anion, admixed with a pharmaceutical vehicle, wherein said pharmaceutical vehicle comprises an inert carrier and a surface active agent in which said compound is dissolved or a solid inert carrier.

2. A pharmaceutical compound as set forth in claim 1, wherein n is 2.

3. A pharmaceutical composition as set forth in claim 1, wherein X is a halide.

4. A pharmaceutical preparation as set forth in claim 1 wherein said compound is 2-(1-adamantanecarbonyloxy)ethyldimethyldodecyl ammonium bromide.

5. A pharmaceutical preparation as set forth in claim 1 wherein said compound is 2-(1-adamantanecarbonyloxy) ethyldimethyltetradecyl ammonium bromide.

6. An anti-microbial oral preparation comprising about 0.1–5% by weight of a chemical compound having the structural formula

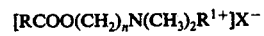

wherein R is 1-adamantyl, $R^1$ is a long chain alkyl group of 10 to 18 carbon atoms, n is an integer from 1 to 3 as X is a compatible anion, admixed with an oral vehicle, which oral vehical comprises a water-insoluble dental polishing material or an aqueous alcohol.

* * * * *